United States Patent [19]

Martinez et al.

[11] Patent Number: 5,310,094
[45] Date of Patent: May 10, 1994

[54] PRESERVATIVE FREE STERILE FLUID DISPENSING SYSTEM

[75] Inventors: F. Jesus Martinez, Mission Viejo; Steven R. Bystrom, El Toro; Peter W. Chan, Northridge, all of Calif.

[73] Assignee: JSP Partners, L.P., Northridge, Calif.

[21] Appl. No.: 792,989
[22] Filed: Nov. 15, 1991
[51] Int. Cl.⁵ .............................. B65D 37/00
[52] U.S. Cl. .................. 222/212; 137/512; 137/846; 222/476; 222/494
[58] Field of Search ........... 222/189, 212, 215, 476, 222/494; 137/512, 846, 849

[56] References Cited

U.S. PATENT DOCUMENTS

| | | | |
|---|---|---|---|
| 2,594,318 | 4/1952 | Langdon | 137/846 X |
| 2,761,833 | 9/1956 | Ward | 222/189 X |
| 2,783,091 | 2/1957 | Haldy | 222/189 |
| 3,034,731 | 5/1962 | Chapin | 137/849 X |
| 3,176,883 | 4/1965 | Davis, Jr. | 222/211 X |
| 3,365,240 | 1/1968 | Gordon | 222/494 X |
| 3,572,375 | 3/1971 | Rosenberg | 137/512 |
| 4,139,469 | 2/1979 | Rainin et al. | 137/512 X |
| 4,349,134 | 9/1982 | Schuster et al. | 222/562 X |
| 4,432,496 | 2/1984 | Ito | 222/189 X |
| 4,475,274 | 10/1984 | Beckstrom et al. | 222/562 X |
| 4,676,407 | 6/1987 | Rideout | 222/562 X |
| 4,776,495 | 10/1988 | Vignot | 222/494 X |
| 4,785,978 | 11/1988 | Kano et al. | 222/494 X |
| 4,938,389 | 7/1990 | Rossi et al. | 222/189 |
| 4,953,588 | 9/1990 | Sands | 137/512.3 |
| 4,978,036 | 12/1990 | Burd | 222/494 X |
| 5,074,440 | 12/1991 | Clements et al. | 222/189 |
| 5,099,885 | 3/1992 | Nilsson | 222/494 X |
| 5,165,573 | 11/1992 | Kuboshima | 222/562 X |
| 5,183,184 | 2/1993 | Ranaletta et al. | 222/189 |

FOREIGN PATENT DOCUMENTS

| | | |
|---|---|---|
| 0117016 | 1/1984 | European Pat. Off. . |
| 0234607 | 1/1987 | European Pat. Off. . |
| 0280669 | 2/1988 | European Pat. Off. . |
| 0305003 | 8/1988 | European Pat. Off. . |
| 0363172 | 10/1989 | European Pat. Off. . |
| 0401022 | 5/1990 | European Pat. Off. . |
| 0452196 | 4/1991 | European Pat. Off. . |
| 0459498 | 5/1991 | European Pat. Off. . |
| 0500249 | 2/1992 | European Pat. Off. . |
| 2405687 | 2/1974 | Fed. Rep. of Germany . |
| 2700970 | 1/1977 | Fed. Rep. of Germany . |
| 3305898 | 2/1983 | Fed. Rep. of Germany . |
| 4008442 | 3/1990 | Fed. Rep. of Germany . |
| 4027539 | 8/1990 | Fed. Rep. of Germany . |
| 2203752 | 10/1973 | France . |
| 2364168 | 9/1976 | France . |
| 2419873 | 3/1978 | France . |
| 2494603 | 11/1980 | France . |
| 2543920 | 4/1983 | France . |
| 2671538 | 1/1991 | France . |
| PCT/US89/04255 | 9/1989 | PCT Int'l Appl. . |
| PCT/CA91/00056 | 2/1991 | PCT Int'l Appl. . |
| PCT/US91/04891 | 7/1991 | PCT Int'l Appl. . |
| PCT/US92/00297 | 1/1992 | PCT Int'l Appl. . |
| PCT/US92/01809 | 3/1992 | PCT Int'l Appl. . |
| PCT/DE92/00489 | 6/1992 | PCT Int'l Appl. . |
| 2021429 | 4/1979 | United Kingdom . |
| 2048827 | 4/1980 | United Kingdom . |
| 2106877 | 8/1982 | United Kingdom . |
| 2158049 | 4/1985 | United Kingdom . |
| 2235038 | 6/1990 | United Kingdom . |
| 2234965 | 2/1991 | United Kingdom . |
| 2260535 | 10/1992 | United Kingdom . |

Primary Examiner—Andres Kashnikow
Assistant Examiner—J. A. Kaufman
Attorney, Agent, or Firm—Robbins, Berliner & Carson

[57] ABSTRACT

A fluid dispensing system for delivering sterile preservative free solution is disclosed. The system uses double self-sealing valves mounted in series inside a tip compartment which fits on the outlet of a multiple dosage squeeze container to prevent undesirable retrograde flow of the dispensed liquid back into the bottle during the decompression cycle. The valves used are positive acting, normally closed duckbill valves which open to express solution from the container when squeezing pressure is applied to the bottle and which automatically close when the pressure is released. A hydrophobic filter is provided to sterilize the replacement air which enters the container upon release of the squeezing pressure.

19 Claims, 1 Drawing Sheet

PRESERVATIVE FREE STERILE FLUID DISPENSING SYSTEM

BACKGROUND OF THE INVENTION

1. Field of the Invention

The present invention relates to a fluid dispensing system specifically designed to deliver multidose sterile, or homogenized and pasteurized, chemical preservative, antibacterial or antimicrobial additive free (hereinafter known collectively as "preservative free") solutions. More, specifically, the present invention is directed to a fluid dispensing system with a dual self-sealing valve system to dispense multidose sterile solutions in a dropwise form. The dual self-sealing valve system and hydrophobic air filter protects the solutions from contamination after multidose dispensing without the use of preservatives.

2. Description of the Prior Art

Large number of solutions including those that are sold and administered as over-the-counter ("OTC") and/or prescription preparations, such as ophthalmic pharmaceutical, contact lens solutions, drop-administrated medicines for the ear or nose, and some consumer health care liquid solutions, such as creams, gels and lotions, must be kept sterile to prevent contamination from bacteria or other microbes. The conventional means of preventing such contamination is to add a preservative or other antibacterial agent to the solution during packaging. Commonly used preservatives include benzalkonium chloride, methyl parabens, propyl parabens, thimerosal and chlorobutanol. Commonly used antibacterial agents include saline formulations. While these preservatives keep the enclosed solution sterile, the bottle itself may harbor external bacterial or microbial growth which is carried along with the outflow of fluids. In addition, the preservatives themselves are often toxic, not just to bacteria or microbes, but also to the cells which are being treated by the bottled solution. For example, the preservatives used in most eye drops can disrupt the corneal epithelium, irritate conjunctival tissues and cause allergic reactions. Because of this toxicity level, continued use can cause more long-term problems than the solutions solve.

Furthermore, squeezable dispensing bottles containing saline formulations in the dispensing liquids may be provided with nozzles including filter membranes which are permeable to the dispensed liquid as well as being permeable to the air which must be aspirated through the nozzle to replace the dispensed liquid and reinflate or re-expand the container. However, the filter membrane must be impermeable to bacteria in order to prevent the aspirated air from carrying bacteria into contact with the stored solution, and contaminating the solution due to repeated dispensing. Yet, filter membrane materials which are sufficiently hydrophilic to permit permeation of the saline solution often permit retention of the saline solution on the filter so that the retained solution increases the resistance of the filter to passage of the aspirating air. The partially obstructed flow of aspirating air not only retards the re-expansion of the squeezed bottle wall, but also impedes repeated squeezing of the bottle when large quantities of the solution must be dispensed. When portions of the filter are treated to repel the solution and improve air passage, the solution can sometimes leach the treating composition from the filter.

In addition, consumer food products, such as milk and dairy products, must be kept refrigerated to reduce the contamination and/or action of bacteria or other microbes.

Container contamination can also be the result of particulate matter being drawn back into the container with the liquid in the dropper tip that has not been delivered as a drop. Over several drop deliveries, for example, in dusty conditions, a significant accumulation of dust in the container is possible.

Despite these and other problems with filter bottles, and the use of preservatives in dispensing liquids, various designs for liquid dispenser for sterile solutions have been reported.

U.S. Pat. No. 4,938,389 describes a dispenser including a filter assembly having a hydrophobic filter and a hydrophilic filter in tandem with the hydrophobic filter located near the dispensing tip.

U.S. Pat. No. 3,760,987 describes a snap assembled dispensing package and cover made up of a container which has a tapered shank on its discharge end and a piercing device, snappably connected to the container, which also serves as a conduit for dispensing the medicament. The dispensing package further contains an air filter and a solution filter.

U.S. Pat. Nos. 4,917,271 and 3,149,758, and WO 90/15015 all teach dispensing devices with single filtering membranes or composite membranes where a portion of the membrane is hydrophobic and another portion of the membrane hydrophilic.

U.S. Pat. No. 4,463,880 describes a medicine drop dispenser with a single hydrophobic and microporous antibacterial filter that provide a barrier to the ingress of bacteria and for permitting the egress of sterile liquid.

U.S. Pat. No. 4,533,068 describes sterile solution delivery and venting devices including a positive acting, normally closed check valve which opens to express solution from the package when squeezing pressure is applied and which automatically closes when the pressure is released. A hydrophobic filter is included to sterilize the replacement air which enters the package upon release of the squeezing pressure.

U.S. Pat. No. 2,684,789 describes seal cap and dispensing nozzle for tubes or bottles having a self-closing dispensing valve.

U.S. Pat. No. 3,176,883 describes a fluid dispenser of the squeeze bottle type having an air vent post extending to the side of the dropper tip and directly above the lip of the container.

U.S. Pat. Nos. 4,739,906, 4,234,103 and 4,773,551 all describe bottles with caps containing a protuberance for closing the hole in the dropper tip.

It would be desirable to provide a convenient, economical and safe fluid dispensing system for the delivery of sterile preservative free solutions.

Accordingly, it is an object of the present invention to provide an improved sterile solution delivery and fluid dispensing system of the type set forth.

It is a another object of the present invention to provide a multidose fluid dispensing system which can protect the solutions from contamination under prolonged and repeated use without the use of preservatives.

It is another object of the present invention to provide a multidose fluid dispensing bottle for dispensing ophthalmic pharmaceutical, contact lens solutions, consumer health care liquid solutions and consumer food product solutions which provide good flow properties and protection against bacterial or microbial contamination.

Another object of the present invention is to provide a multidose fluid dispensing bottle which can be used to dispense medicine solutions, which do not contain preservatives, in substantially uniform drops.

It is another object of the present invention to provide a novel fluid dispensing system which incorporates positive acting, normally closed, valve means in combination with a hydrophobic membrane air sterilizing filter means.

It is another object of the present invention to provide a novel fluid dispensing system which incorporates two positive acting, normally closed, valve means in series and in combination with a hydrophobic membrane air sterilizing filter means.

It is another object of the present invention to provide a novel fluid dispensing system having a container with a system outlet and an air passageway, positive acting, normally closed, valve means positioned between the system fluid outlet and a hydrophobic filter positioned at the end of the air inlet passageway, the valves means being openable upon the application of pressure built up within the container and being automatically sealed upon release of the pressure.

Other objects and advantages of the invention will become apparent from the following detailed disclosure.

SUMMARY OF THE INVENTION

In accordance with the present invention, a preservative free sterile solution dispensing system is provided to eliminate the need of using preservatives in ophthalmic, pharmaceutical, contact lens solutions, consumer health care liquids and consumer food product solutions. The fluid dispensing system for dispensing sterile preservative free solution comprises a container having an outer and an inner surface. The container further has a reservoir compartment for storing sterile solution and a tip compartment adapted to dispense the sterile solutions. A dual self-sealing valve dispensing assembly is sealed by an adhesive, mechanical compression, ultrasonic sealing, gasket, encapsulation or other commonly known methods, to the inside surface of the tip compartment and comprises a hydrophobic membrane assembly having a membrane housing. The membrane housing is constructed of a thermoplastic material, such as polyethylene, polypropylene, polystyrene, ethylene-vinyl acetate or a combination thereof. A hydrophobic membrane support is connected to the membrane housing. The hydrophobic membrane support has a top surface and a bottom surface. The hydrophobic membrane support further has a central fluid channel to allow the solution to pass through. The hydrophobic membrane support is also generally constructed of a thermoplastic material such as polyethylene, polypropylene, polystyrene, ethylene-vinyl acetate or a combination thereof. A hydrophobic membrane is hermetically sealed to the bottom surface of the hydrophobic membrane support separating the reservoir compartment from the tip compartment. The membrane further connects to a central solution flow port which in turn is in communication with the fluid channel in the hydrophobic membrane support to allow the solution to pass through. The hydrophobic membrane is constructed of a hydrophobic polymer, such as polyfluoroethylene, including TEFLON ®, polyolefins or a combination thereof. A passageway for ingress of air from outside the container through the membrane is provided in the hydrophobic membrane support. The dual self-sealing valve dispensing assembly further comprises a valve assembly, which in turn, comprises a valve housing support with a top and a bottom surface. The bottom surface of the valve housing support further connects to the top surface of the hydrophobic membrane support; a first self-sealing valve is hermetically sealed to the bottom surface of the housing support; a second self-sealing valve is hermetically sealed to the top surface of the valve housing support and in series with the first self-sealing valve wherein an outlet of the first valve opens to an inlet of the second valve to allow the solution to pass through; and a system outlet from which solution from an outlet of the second valve passes through.

BRIEF DESCRIPTION OF THE DRAWING

The novel features which are believed to be characteristic of the invention are set forth with particularity in the appended claims. The invention itself, however, both as to its organization and method of construction and operation, may best be understood by reference to the following description, taken in connection with the accompanying drawing in which:

DESCRIPTION OF THE PREFERRED EMBODIMENT

Figure 1:
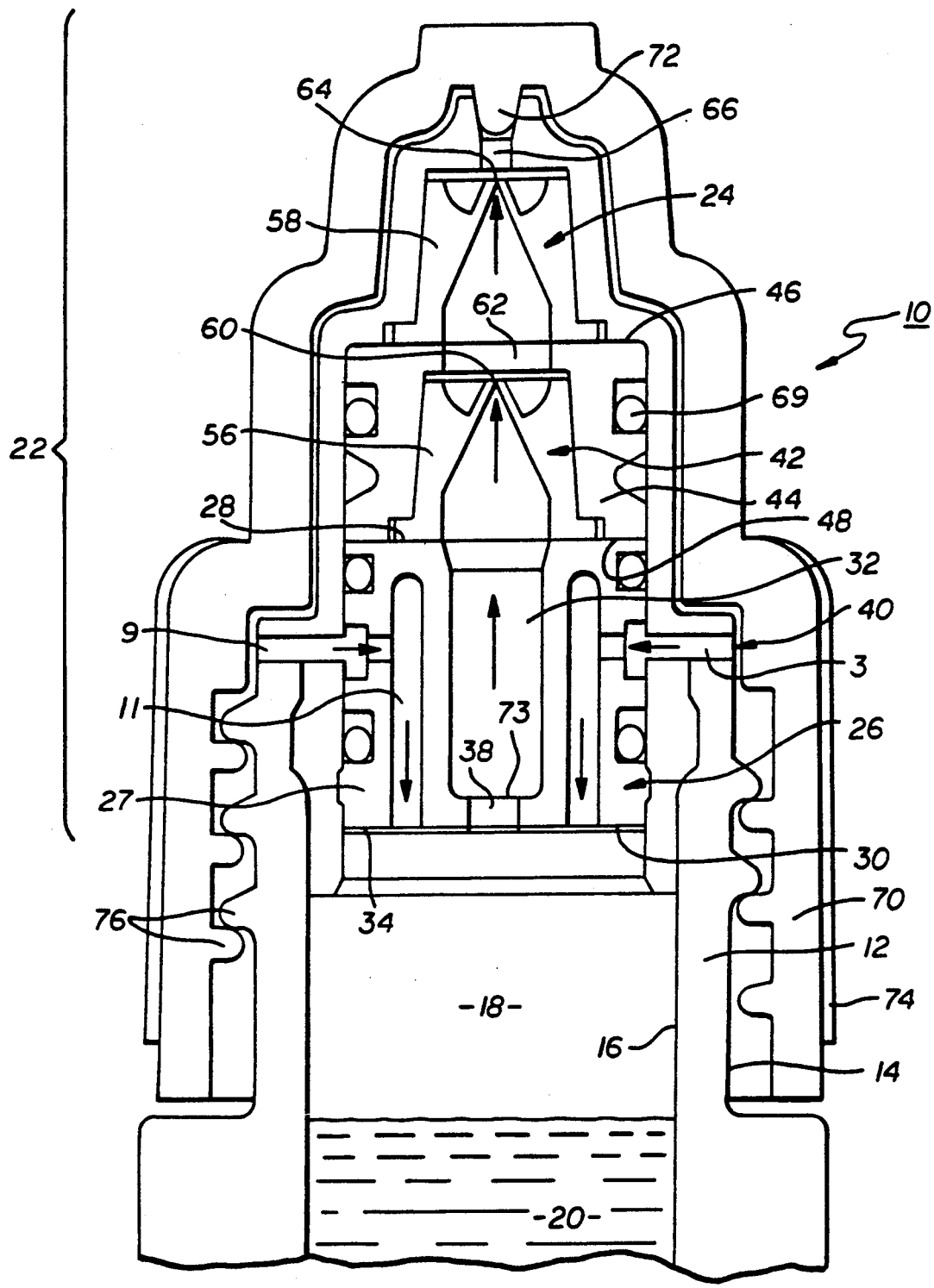
FIG. 1 is a perspective cross-sectional view of a preservative free sterile fluid dispensing system of the present invention.

Referring now to FIG. 1, the preservative free fluid dispensing system 10 is provided with a container 12 having an outer surface 14 and an inner surface 16. The container 12 is provided with means to temporarily reduce its volume, typically by providing that at least part of the container is elastically deformable. Thus, pressure on a deformable portion of the container will force the fluid contained therein out of the container when it is appropriately oriented. The container 12 can be a standard dispersing bottles with removable tip, e.g., low density polypropylene such as those made by Wheaton Plastics, Melville, N.J.

The container 12 further has a reservoir compartment 18 for storing sterile solution 20 and a tip compartment 22 adapted to dispense the sterile solution 20. A dual self-sealing valve dispensing assembly 24 is sealed to the inside surface 16 of the container 12. The dual self-sealing valve dispensing assembly 24 has a membrane housing 26 to which hydrophobic membrane support 27 with a top surface 28 and a bottom surface 30 is attached. The hydrophobic membrane support 27 further has a central fluid channel 32 for the solution 20 to pass through. A hydrophobic membrane 34 is hermetically sealed to the bottom surface 30 of the hydrophobic membrane support 27, separating the reservoir compartment 18 from the tip compartment 22 except at a central solution flow port 38 which is in communication with the fluid channel 32 of the hydrophobic membrane support to allow the solution 20 to pass through. The hydrophobic membrane support 27 also has a passageway 40 (comprising an inflow 3, side port 9 and channel 11 discussed below) for ingress of air from outside the container 12 through the membrane 34. The hydrophobic membrane 34 has pore openings from 0.01 to 1 micron, and preferably about 0.2 to 0.24 micron, in flat sheet configuration. Such hydrophobic membranes are readily available commercially and can be fabricated from any suitable hydrophobic polymer, such as tetrafluoroethylene, polyolefins, including polyethylene and polypropylene or a mixture thereof. In the preferred example, the hydrophobic membrane is a laminated tetrafluoroethylene (e.g. TEFLON®, a trademark of E. I. du Pont de Nemours Co.) membrane obtained from W. L. Gore, Inc. and has a pore size of about 0.2 to about 0.24 microns and preferably about 0.22 microns. Since the hydrophobic membrane is used to separate the reservoir compartment 18 from the tip compartment 22, it has a surface area of about 0.1 to about 0.2 $cm^2$ and preferably about 0.13 $cm^2$. The dual self-sealing valve dispensing assembly 24 further has a valve assembly 42 comprising a valve housing 44 with a top surface 46 and a bottom surface 48 and sealed by gasket to the top surface 28 of the hydrophobic membrane support 27. A first self-sealing valve 56 is hermetically sealed to the bottom surface 48 of the valve support 44. A second self-sealing valve 58 is similarly hermetically sealed to the top surface 46 of the valve housing support 44 and in series with the first self-sealing valve 5 wherein the outlet 60 of the first valve opens to an inlet 62 of the second valve to allow solution to pass through. Solution 20, after passing through the outlet 64 of the second self-sealing valve 58, then dispenses to the outside of the container 12 via system outlet 66. The first and second self-sealing valves used are generally of the duckbill type and are normally closed during storage. The self-sealing valves used in the preferred embodiment are of the duckbill type, model X60Z9 and can be obtained from Vernay Laboratories, Inc. The outlet 64 from the second self-sealing valve opens to a system outlet 66 from which the solution 20 is dispensed. In a preferred embodiment, elements 26 (system housing), hydrophobic membrane support 27, valve housing support 44, second self-sealing valve 56 and gasket 69 (in the form of 0-rings), all coact to form a hermetically tight assembly with container 12.

After assembly, during a dispensing cycle, bottle 12 is squeezed in an inverted position with sterile solution 20 flowing from the reservoir compartment, through the central solution flow port 38, and percolate through hydrophobic membrane 73, channel 32 in the center of hydrophobic membrane support 27, through the first self-sealing valve 56 and outlet 60 of same, through inlet 62 and outlet 64 of second self-sealing valve 58 and finally out through system outlet 66 of container 12. To minimize contamination by reducing exposure to outside aerial bacteria or microbes, the system outlet 66 is of a dimension of only about 0.050 to about 0.127 cm. Once the solution is discharged from container 12, pressure equilibrium during the decompression stage is obtained by the inflow of room air 3 through side port 9 of housing 26 and channel 11 of hydrophobic membrane support 27. The air is then filtered and rendered sterile by hydrophobic membrane 34.

Protection of the external surface 14 of the container tip compartment 22 is achieved by means of a cap 70 with bayonet extension 72 which hermetically seals the outlet of the fluid dispensing system upon closure. The cap further is provided with antislip knurls 74 which are threaded together by means of threads 76. In addition, the cap 70 can be rendered bactericidal and bacteriostatic by further impregnating the plastic material with an antibacterial agent such as salts of common heavy metal oxides, including oxides of silver, gold or copper.

EXAMPLES

The performance of the dual self-sealing valve dispensing assembly was tested under the following conditions:

Example 1. Dye Diffusion Tests

A 5% aqueous solution of food grade blue dye was prepared from a stock concentrate. Fifteen double duckbill self-sealing valve dispensing assemblies in their normally closed position were connected in parallel on a tubing set testing fixture. The entire tubing set was primed with the dye solution and the dual double duckbill self-sealing valve assemblies connected to each of the parallel tubing arms. A calibrated pressure gauge connected to the tubing assembly was used to monitor the hydraulic pressure continuously for 24 hours. After 24 hours exposure to a pressure of 20 mm Hg, no retrograde migration of dye was detected past the first or second duckbill valve by direct observation and by colorimetric determination. When samples of the self-sealing double duckbill assembly were subjected to 24 hours exposure under 160 mm Hg external pressure (about 10 times greater than normally expected during the bottle decompression cycle), no retrograde dye migration was observed past the first or second self-sealing duckbill valves. When samples with the duckbill valve closer to the dispensing tip outlet were purposely damaged and tested under the same conditions as above, the second self-sealing duckbill valve prevented retrograde migration of dye past the normally closed seal surface.

Example 2. Double Duckbill Back Flow Air Pressure Integrity Tests

Fifteen double duckbill self-sealing valve dispensing assemblies were inserted into the outlet of standard Wheaton squeeze bottles containing 15 ml of water. To each unit, a "T" tubing assembly containing a pre-calibrated pressure gauge and a compressed air source was connected to the dispensing tip outlets. The self-sealing double duckbill valve assemblies were subjected to an air pressure of 160 mm Hg for 90 seconds and isolated from the air pressure source by cross clamping the tubing. With the squeeze bottle inverted, no air bubbles were detected entering the water contained within the bottle while the pressure gauge reading remained constant.

Example 3. Hydrophobic Membrane Air Venting Tests

Fifteen Wheaton bottles containing 15 ml of water were each equipped with double duckbill self-sealing valve dispensing assemblies and integrity tested for leaks. The valve assemblies were provided with a freshly mounted hydrophobic membrane disc measuring 8 mm in diameter and hermetically sealed to a holder on two separate, but concentric sealing surfaces. The hydrophobic disc contained a functional surface area of 0.13 $cm^2$ and 0.2 micron pore size. The hydrophobic membrane discs had not been exposed to water before the tests. During the tests, the squeeze bottles were inverted and hand squeezed until 5 drops to 3–4 ml of water were expelled through the double duckbill valves and tip assembly. Upon release of the squeezing external pressure on the sides of the bottles, the differential negative pressure created within the bottles was sufficient to allow air in the form of bubbles to filter through the hydrophobic membrane into the inverted bottle. Depending on the amount of water expelled from the bottle, pressure equalization required from 2 seconds to 10 seconds. The same results were obtained when the bottle was set in the upright position.

Example 4. Hydrophobic Membrane Air Venting Tests

The same conditions as in Example 3 except that the hydrophobic membrane discs in all fifteen double duckbill valve assemblies were immersed in water at room temperature for 24 hours. The ability of the hydrophobic membrane discs to filter air entering the bottle was similar to the results obtained with the hydrophobic membrane never exposed to water.

Example 5. Bottle Cap Bayonet Seal Integrity Tests

Fifteen Wheaton squeeze bottles completely filled with water and equipped with double duckbill valve assemblies were each hermetically sealed by intrusion of the bayonet of the bottle cap into the dropper tip opening and hand tightening the cap on the bottle with the usual twisting force. With each bottle in an inverted position, the bayonet seal was challenged with two to three times the positive liquid pressure than is normally expected for a total of 90 seconds. After the integrity pressure test, each bottle was set in an upright position and the cap removed and examined for the presence of water inside the cap well. In each of the assemblies no water was found. The bayonet in the screw-on bottle cap coacting with the mating surface on the dispensing tip hermetically sealed the outlet channel on the dispensing tip assembly.

Example 6. Sterility Test

After the sterile fluid dispensing system 10 with a hydrophobic membrane air filter 34 and dual self-sealing valve dispensing assembly 24 in the preferred embodiments of the present invention was tested with Pseudomonas Diminuta to a population of 10 million per milliliter (HIMA challenge), the bacterial retentivity of the membranes and the double self-sealing valving system met a sterility grade barrier.

Those skilled in the art will fully appreciate that the present embodiment shown and desirable to illustrate the present invention is exemplary only and that the same principles may be employed in providing other preservative free sterile fluid dispensing systems. It will be further appreciated that various other minor modifications or changes, particularly with respect to details of component construction, might be made without departing from the gist and essence of the invention. Accordingly, it should be interpreted as encompassing all component constructions fairly regardable as functional equivalents of the subject matter to which claims are directed.

Having described our invention, what we claim and desire to secure by letter patent is:

1. A fluid dispensing system for dispensing sterile preservative free solution comprising:
   a container having an outer surface and an inner surface;
   said container further having a reservoir compartment for storing a sterile solution and a tip compartment adapted to dispense the sterile solution;
   said container further having at least part of it elastically deformable;
   a dual self-sealing valve dispensing assembly sealed to the inside surface of said tip compartment;
   wherein said dual self-sealing valve dispensing assembly further comprises:
   a membrane assembly having a membrane housing;
   a hydrophobic membrane support connected to said membrane housing;
   said hydrophobic membrane support further having a top surface, a bottom surface and a central fluid channel to allow the sterile solution to pass through;
   a hydrophobic membrane hermetically sealed to said bottom surface of said hydrophobic membrane support separating said reservoir compartment from said tip compartment, said membrane further connected to a central solution flow port which in turn communicates with said fluid channel of said hydrophobic membrane support to allow the solution to pass through;
   a passageway located in said hydrophobic membrane support for ingress of air from outside said container through said hydrophobic membrane;
   a valve assembly comprising a vale housing support with a top surface and a bottom surface;
   said bottom surface of said valve housing support further connected to said top surface of said hydrophobic membrane support;
   a first self-sealing valve hermetically sealed to said bottom surface of said housing support;
   a second self-sealing valve hermetically sealed to said top surface of said valve housing support and in series with said first self-sealing valve wherein an outlet of said first valve opened to an inlet of said second valve to allow the solution to pass through; and
   a system outlet from which the solution from an outlet of said second valve passes through.

2. A fluid dispensing system of claim 1, wherein said membrane housing is constructed of a thermoplastic material.

3. A fluid dispensing system of claim 2, wherein said thermoplastic material is selected from the group consisting of polyethylene, polypropylene, polystyrene, ethylene-vinyl acetate and combinations thereof.

4. A fluid dispensing system of claim 2, wherein said hydrophobic support is constructed of a thermoplastic material.

5. A fluid dispensing system of claim 4, wherein said thermoplastic material is selected from the group consisting of polyethylene, polypropylene, polystyrene, ethylene-vinyl acetate and combinations thereof.

6. A fluid dispensing system of claim 4, wherein said hydrophobic membrane is constructed of a hydrophobic polymer.

7. A fluid dispensing system of claim 6, wherein said hydrophobic polymer is selected from the group consisting of polyfluoroolefins, polyolefins and combinations thereof.

8. A fluid dispensing system of claim 7, wherein said hydrophobic membrane further has a pore size of about 0.01 to about 1 micron.

9. A fluid dispensing system of claim 8, wherein said hydrophobic membrane further has a pore size of about 0.2 to about 0.24 micron.

10. A fluid dispensing system of claim 9, wherein said hydrophobic membrane is suitable for resisting the passage of bacterial and microbial contamination and has a surface area of about 0.1 to about 0.2 cm$^2$.

11. A fluid dispensing system of claim 10, wherein said hydrophobic membrane is suitable for resisting the passage of bacterial and microbial contamination and has a surface area of about 0.13 cm².

12. A fluid dispensing system of claim 9, wherein said housing support is constructed of polyolefins and combinations thereof.

13. A fluid dispensing means of claim 12, wherein said first-sealing valve is a normally closed deformable duckbill valve.

14. A fluid dispensing system of claim 13, wherein said second sealing valve is a normally closed deformable duckbill valve.

15. A fluid dispensing system of claim 14, wherein said system outlet is further provided with a cap having bayonet extension means which displaces residual fluid and hermetically seals said outlet upon closure.

16. A fluid dispensing system of claim 15, wherein said cap is further provided with antislip knurls and threads for sealing to said outlet.

17. A fluid dispensing system of claim 15, wherein said cap is further rendered bactericidal and bacteriostatic with an agent selected from the group consisting of sliver oxide, gold oxide and copper oxide.

18. A fluid dispensing system of claim 14, wherein said system outlet is of a dimension of about 0.050 to about 0.127 cm.

19. A fluid dispensing system for dispensing sterile, preservative-free solutions comprising:
   a container having at least part of it elastically deformable;
   said container further having an outer surface and an inner surface;
   said container further having a reservoir compartment for storing a sterile solution and a tip compartment adapted to dispense the sterile solution;
   a dual self-sealing valve dispensing assembly sealed to the inside surface of said tip compartment;
   said dual self-sealing valve dispensing assembly further comprising:
      a membrane assembly having a polyethylene membrane housing;
      a polyethylene hydrophobic membrane support connected to said polyethylene membrane housing;
      said polyethylene hydrophobic membrane support further having a top surface, a bottom surface and a central fluid channel to allow the sterile solution to pass through;
      a tetrafluoroethylene polymer hydrophobic membrane hermetically sealed to said bottom surface of said polyethylene hydrophobic membrane support separating said reservoir compartment from said tip compartment;
      said tetrafluoroethylene polymer hydrophobic membrane further being connected to a central solution flow port which in turn communicates with said fluid channel of said hydrophobic membrane support to allow the solution to pass through;
      said tetrafluoroethylene polymer hydrophobic membrane further having a pore size of about 0.22 micron and a surface area of about 0.13 cm²;
      a passageway located in said hydrophobic membrane support for ingress of air from outside said container through said tetrafluoroethylene polymer hydrophobic membrane;
      a valve assembly comprising a valve housing support with a top surface and a bottom surface;
      said bottom surface of said valve housing support further connecting to said top surface of said hydrophobic membrane support;
      a first normally closed deformable self-sealing duckbill valve hermetically sealed to said bottom surface of said housing support;
      a second normally closed deformable self-sealing duckbill valve hermetically sealed to said top surface of said valve housing support and in series with said first normally closed deformable self-sealing duckbill valve wherein an outlet of said first normally closed deformable self-sealing duckbill valve opens to an outlet of said second normally closed deformable self-sealing duckbill valve to allow the solution to pass through; and
   a system outlet of a dimension of about 0.050 to about 0.127 cm from which the solution from an outlet of said second normally closed deformable self-sealing duckbill valve passes through.

* * * * *

UNITED STATES PATENT AND TRADEMARK OFFICE
CERTIFICATE OF CORRECTION

PATENT NO. : 5,310,094

DATED : May 10, 1994

INVENTOR(S) : F. Jesus Martinez, Steven R. Bystrom & Peter W. Chan

It is certified that error appears in the above-identified patent and that said Letters Patent is hereby corrected as shown below:

```
Column 5, line 22, replace "5" with --56--.
Column 8, line 21, replace "a vale" with --a valve--.
```

Signed and Sealed this

Thirtieth Day of August, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,310,094
DATED : May 10, 1994
INVENTOR(S) : F. Jesus Martinez, Steven R. Bystrom & Peter W. Chan It is certified that error appears in the above-indentified patent and that said Letters Patent is hereby corrected as shown below:

Column 5, line 31, replace "X60Z9" with --X6079--.

Signed and Sealed this

Twentieth Day of December, 1994

Attest:

BRUCE LEHMAN

*Attesting Officer*      *Commissioner of Patents and Trademarks*